United States Patent
West

(10) Patent No.: US 8,417,318 B2
(45) Date of Patent: Apr. 9, 2013

(54) CALIBRATING TRACKING SYSTEMS TO REMOVE POSITION-DEPENDENT BIAS

(75) Inventor: Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1455 days.

(21) Appl. No.: 11/710,729

(22) Filed: Feb. 22, 2007

(65) Prior Publication Data

US 2008/0202200 A1 Aug. 28, 2008

(51) Int. Cl.
*A61B 5/05* (2006.01)
(52) U.S. Cl. .................................................. 600/424
(58) Field of Classification Search ..................... None
See application file for complete search history.

(56) References Cited

U.S. PATENT DOCUMENTS

| | | | | |
|---|---|---|---|---|
| 5,517,016 A | * | 5/1996 | Lesh et al. | 250/201.1 |
| 5,579,444 A | * | 11/1996 | Dalziel et al. | 700/259 |
| 6,307,914 B1 | | 10/2001 | Kunieda et al. | |
| 2002/0099677 A1 | * | 7/2002 | Calise et al. | 706/23 |
| 2005/0085714 A1 | * | 4/2005 | Foley et al. | 600/424 |

OTHER PUBLICATIONS

Derek L.G. Hill et al., "Registration Methodology: Concepts and Algorithms", The Biomedical Engineering Series, Series Editor Michael Neuman Medical Image Registration, Edited by: Joseph V. Hajnal, CRC Press Boca Raton, London, New York, Washington, D.C., Copyright 2001 by CRC Press LLC, 36 pages total.

Jay B. West et al., "Designing Optically Tracked Instruments for Image-Guided Surgery", IEEE Transactions on Medical Imaging, vol. 23, No. 5, May 2004, pp. 533-545.

J. Michael Fitzpatrick et al., "Predicting Error in Rigid-Body Point-Based Registration", IEEE Transactions on Medical Imaging, vol. 17, No. 5, Oct. 1998, pp. 694-702.

Jay B. West, "Predicting Error in Point-Based Registration", (Ph.D. dissertation, Vanderbilt University), (available from Science Library, Vanderbilt University), submitted Sep. 2000, Published 2001, pp. 120 total.

* cited by examiner

*Primary Examiner* — Unsu Jung
*Assistant Examiner* — Saurel J Selkin
(74) *Attorney, Agent, or Firm* — Lowenstein Sandler LLP

(57) ABSTRACT

A method for removing position-dependent bias from tracking systems computes invertible transformations between a tracking system and a reference system, and applies an inverse of the transformation to measurements in the tracking system to estimate the locations of reference points in the reference system and to determine relative bias at the measured points.

10 Claims, 7 Drawing Sheets

CALIBRATING TRACKING SYSTEMS TO REMOVE POSITION-DEPENDENT BIAS

TECHNICAL FIELD

Embodiments of the present invention are related to the calibration of tracking systems and, more particularly, to the correction of position-dependent bias in tracking systems.

BACKGROUND

Image-guided systems designed for neurosurgery, hip surgery, spine surgery and other anatomy that is relatively rigid can use rigid body transformations to accomplish image registration. These systems often rely on point-based registration to determine the transformation, and many such systems use fiducial markers, attached to rigid anatomical features, to establish accurate fiducial points for the registration. Image-guided radiotherapy and radiosurgery systems, for example, may use intra-operative x-ray imaging systems to generate images that can be registered with synthetic x-ray images (digitally reconstructed radiographs, or DRRs) derived from 3-dimensional pre-operative scan data (e.g., computed tomography or magnetic resonance imaging) that is used for treatment planning. Such systems may achieve sub-millimeter accuracy in fiducial registration, but also require that the patient be exposed to x-rays periodically during treatment (e.g., every 5 seconds).

In situations where the patient's total x-ray exposure needs to be limited, or where an invasive surgical procedure requires the presence of a surgeon and operating room personnel, the use of intra-operative x-ray imaging may be severely limited or prohibited. In such situations, x-ray imaging may be replaced or supplemented with an optical or magnetic tracking system. The tracking system is used to track the locations of fiducial markers that are attached to the patient (e.g., directly attached or integrated into a rigid frame that is attached to the patient). If the tracking system is calibrated to the intra-operative imaging system, then locations of the fiducial markers can then be registered with the intra-operative imaging data to insure that the treatment or procedure conforms to the treatment plan.

The tracked locations of the fiducial markers on the patient are used to find a rigid transformation between the coordinate space of the patient on the operating table and the corresponding space in the pre-operative images of the patient, which visualize the same fiducial markers at known locations. The known locations of the fiducial markers may be used to calculate the rotations and translations that best map the coordinate space of the patient to the pre-operative image space. The information can be used to position the patient in the operating room or to position a robotically controlled surgical instrument relative to the patient to conform treatment to a treatment plan based on the pre-operative scan data.

Such tracking systems, however, are subject to measurement error. One component of error is random error, often called noise or jitter. The effects of random error may be reduced by taking many measurements at a given location and averaging the results because random error has an average value of zero. Another component of error is position-dependent bias, which varies over space but remains constant at any given point. Position-dependent bias may be caused, for example, by miscalibrations of lenses in an optical tracking system or local magnetic field distortions in a magnetic tracking system.

BRIEF DESCRIPTION OF THE DRAWINGS

The present invention is illustrated by way of example, and not by limitation, in the figures of the accompanying drawings in which.

DETAILED DESCRIPTION

In the following description, numerous specific details are set forth such as examples of specific components, devices, methods, etc., in order to provide a thorough understanding of embodiments of the present invention. It will be apparent to one skilled in the art, however, that these specific details need not be employed to practice embodiments of the present invention. In other instances, well-known materials or methods have not been described in detail in order to avoid unnecessarily obscuring embodiments of the present invention.

Unless stated otherwise as apparent from the following discussion, it will be appreciated that terms such as "generating," "registering," "determining," "aligning," "positioning," "processing," "computing," "selecting," "estimating," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

In the following description, embodiments of the invention are discussed with reference to a robotic, image-guided radiosurgery system to provide specific examples and to provide clarity in the description. It will be appreciated that embodiments of the invention may be practiced in other types of image-guided systems, including non-robotic, gantry-based radiosurgery and radiotherapy systems, as well as non-medical image-guide systems such as industrial machine-vision systems, for example.

Figure 1:
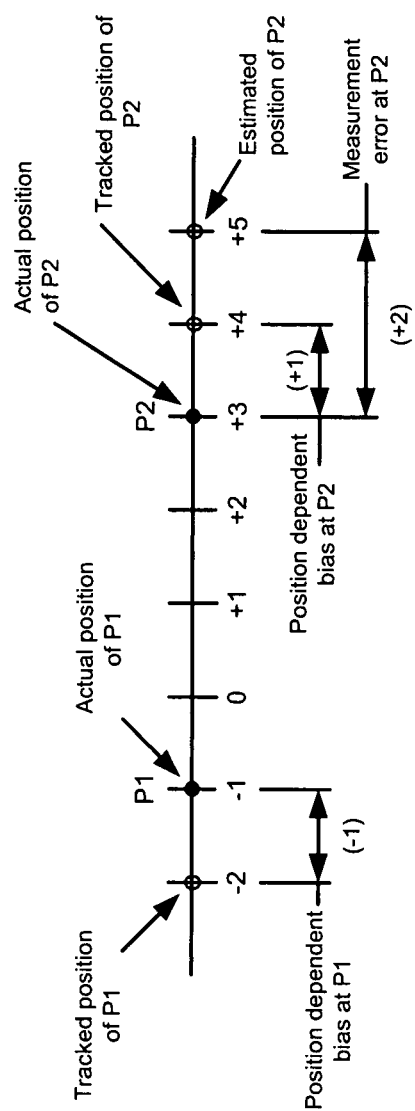
FIG. 1 illustrates position-dependent bias in a one-dimensional tracking system.

FIG. 1 illustrates a problem associated with uncorrected position-dependent bias in a tracking system, using a simple one-dimensional example. In one dimension, the only transformation needed to map between one coordinate space and another is a single translation. In FIG. 1, P1 and P2 are two points having actual positions in a reference coordinate system at −1 and +3, respectively, in some arbitrary units of measurement. In the example illustrated, it is assumed that a tracking system having position-dependent bias is used to measure the positions of P1 and P2. Assuming that there is a bias of −1 in the tracking system at P1, the tracking system would measure the position of P1 as −2. If this bias is assumed to be constant (position-independent), then any subsequent measurement with the tracking system would be corrected by adding +1 (the reverse of the assumed uniform bias) to the measured value to obtain the correct position. For example, if the position of P2 (at +3 in the reference coordinate system) was measured by the tracking system at +4, then the assumption of a uniform bias would result in an estimated position of P2 of +5, resulting in a measurement error of 2 units.

Figure 2:
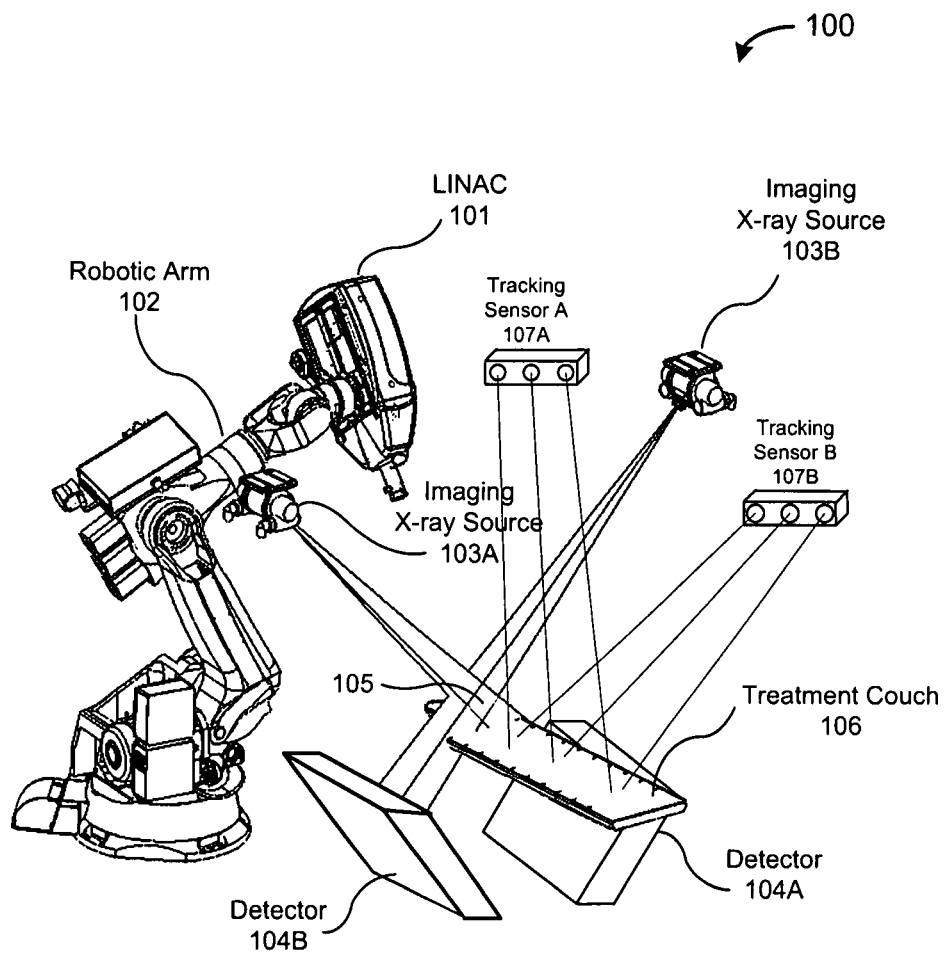
FIG. 2 illustrates an image-guided radiosurgery system including a tracking system in one embodiment.

FIG. 2 illustrates the configuration of an image-guided, robotic-based radiation treatment system 100, such as the CYBERKNIFE® Stereotactic Radiosurgery System manufactured by Accuray Incorporated of Sunnyvale, Calif., that may be used to implement embodiments of the invention. In FIG. 2, the radiation treatment source is a linear accelerator (LINAC) 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient.

The treatment delivery system of FIG. 2 includes an in-treatment (intra-operative) imaging system, which may include x-ray sources 103A and 103B and x-ray detectors (imagers) 104A and 104B. The two x-ray sources 103A and 103B may be aligned to project imaging x-ray beams from two different angular positions (e.g., separated by 90 degrees) to intersect at a machine isocenter 105, which provides a reference point for positioning a patient on a treatment couch 106 during treatment, and to illuminate imaging planes of respective detectors 104A and 104B after passing through the patient. In other embodiments, system 100 may include more than two x-ray sources and more than two detectors. As described in greater detail below, the intra-operative imaging system may be used to establish a reference coordinate system in an operating room in which fiducial markers may be located.

Treatment delivery system 100 may also include tracking sensors 107A and 107B, which may be associated with any type of optical, infrared and/or magnetic tracking system as are known in the art. As noted above, tracking sensors 107A and 107B may be part of a tracking system that replaces and/or supplements the in-treatment x-ray imaging system. As described in greater detail below, tracking sensors 107A and 107B may used to establish a tracking coordinate system in the operating room. In one embodiment, the sensors may be active or passive optical or infrared sensors, for example, in which case the fiducial markers may be passive reflectors or active sources of optical or infrared energy, respectively. In another embodiment, the "sensors" may be magnetic field sources that generate a gradient magnetic field, in which case the fiducial markers may be magnetic field detectors.

Figure 3:
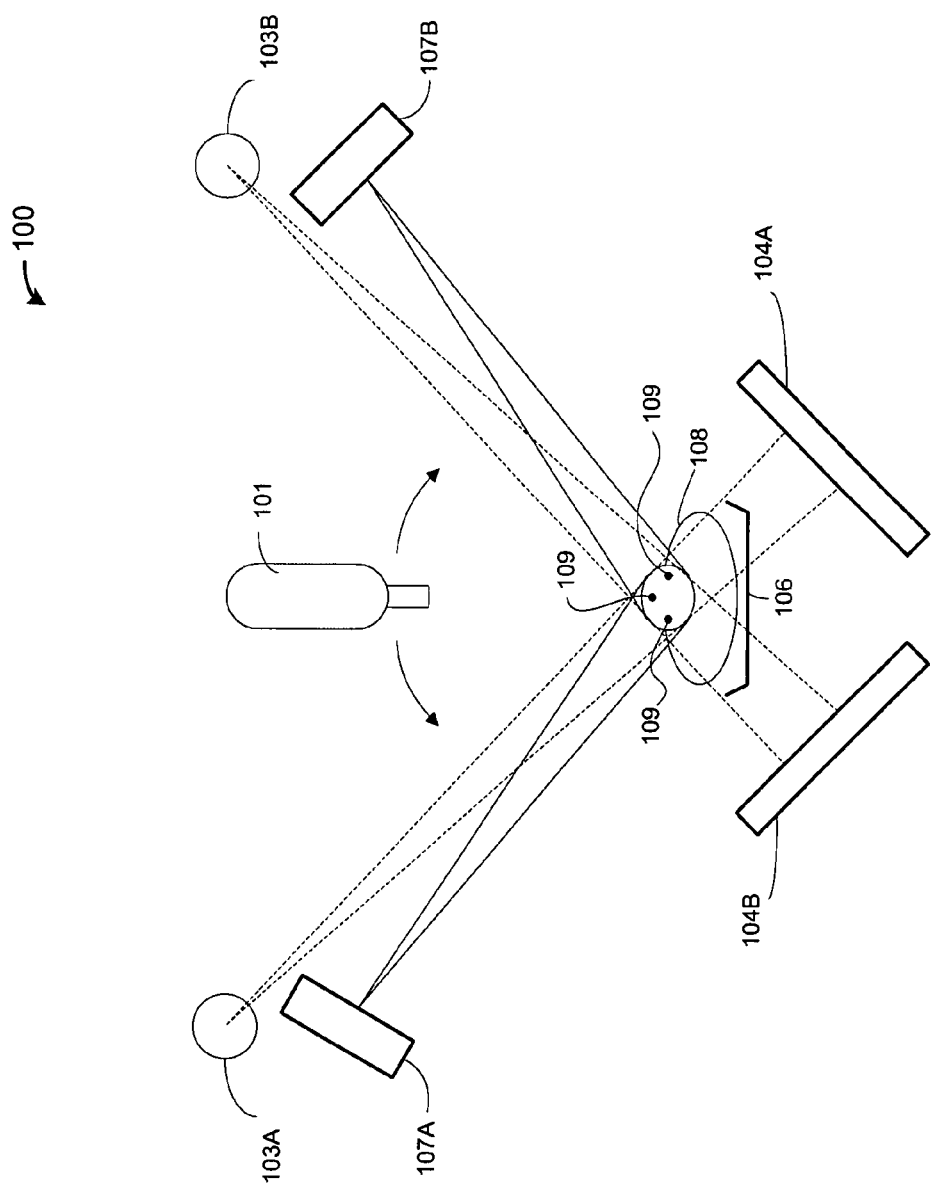
FIG. 3 illustrates a plane view of the image-guided radiosurgery system of FIG. 2 in one embodiment.

FIG. 3 illustrates a plane view of treatment delivery system 100. In FIG. 3, a patient or surgical phantom (i.e., an artificial body with x-ray opacity similar to a human body) 108 with attached fiducial markers 109 is placed within the fields of view of the x-ray imaging system (sources 103A, 103B and detectors 104A, 104B) and the tracking system (tracking sensors 107A, 107B). The x-ray imaging system may be calibrated to a high level of accuracy (e.g., sub-millimeter accuracy) in a reference coordinate system in the operating room, so that an x-ray image of the patient or phantom 108 can be registered with DRRs from pre-treatment scans that include the fiducial markers 109. The tracking coordinate system may then be calibrated with the reference coordinate system to provide registration results between the two systems as described below.

Figure 4:
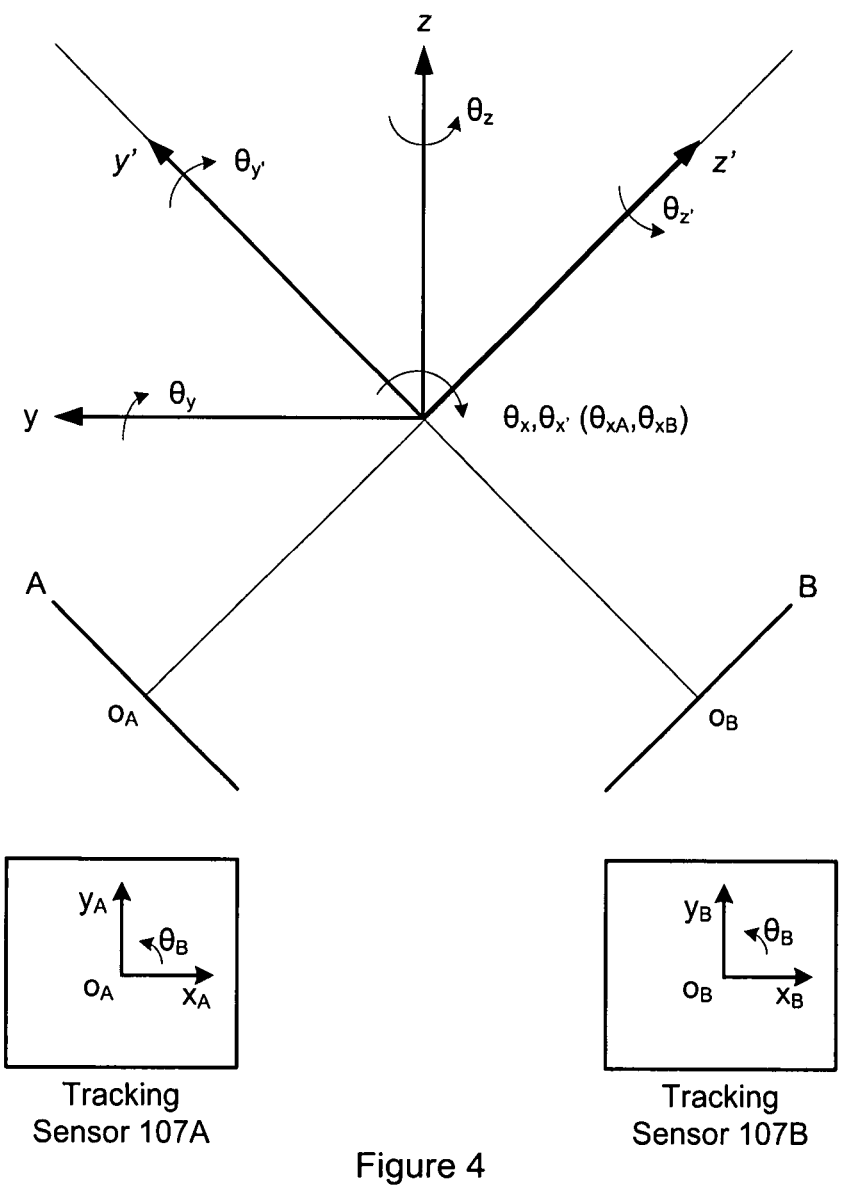
FIG. 4 illustrates the relationship between a reference coordinate system and a tracking coordinate system in one embodiment.

FIG. 4 illustrates the relationship between a reference coordinate system (e.g., the reference coordinate system established by the intra-operative imaging system) and a tracking coordinate system (e.g., the tracking coordinate system established by the tracking sensors 107A and 107B). In FIG. 4, the reference coordinate system is defined by axes x, y and z and the tracking coordinate system is defined by axes x', y' and z' (note that the x and x' axes are shown orthogonal to the plane of FIG. 3 for convenience of illustration, but may in general have arbitrary orientations). To track points in three dimensions, the tracking system requires at least two sensors, each capable of tracking in two dimensions.

A three-dimensional (3D) point-based rigid transformation may be defined from coordinate system xyz to coordinate system x'y'z' in FIG. 4 in terms of three translations ($\Delta x, \Delta y, \Delta z$) and three rotations ($\Delta\theta_x, \Delta\theta_y, \Delta\theta_z$), such that any point in one coordinate system can be mapped into the other coordinate system. In general, at least three fiducial points are required determine a 3D rigid transformation. Point-based rigid transformations are known in the art and, accordingly, are not described here in detail (see, e.g., Derek Hill & Philipe Batchelor, *Registration Methodology: Concepts and Algorithms*, in Medical Image Registration 39-70 (Joseph V. Hajnal et al. eds, 2001). Measures of error in point-based registration include the imprecision in locating the fiducial points (fiducial localization error, FLE), the distance between corresponding fiducial points after registration is performed (fiducial registration error, FRE) and the distance between corresponding target points, other than fiducials (e.g., the desired surgical site), after registration is performed (target registration error, TRE). For a given fiducial localization error (FLE), TRE increases as the distance between the target point and the geometric centroid of the fiducials increase. The following description does not address the issue of deriving and attempting to minimize the component of TRE caused by the random component of FLE; instead, it is concerned only with the component of TRE caused by position dependent bias. Also, although we use the example of a rigid transformation, any invertible transformation may be similarly employed given sufficient fiducials to compute such a transformation between reference and tracking coordinate systems.

Figure 5:
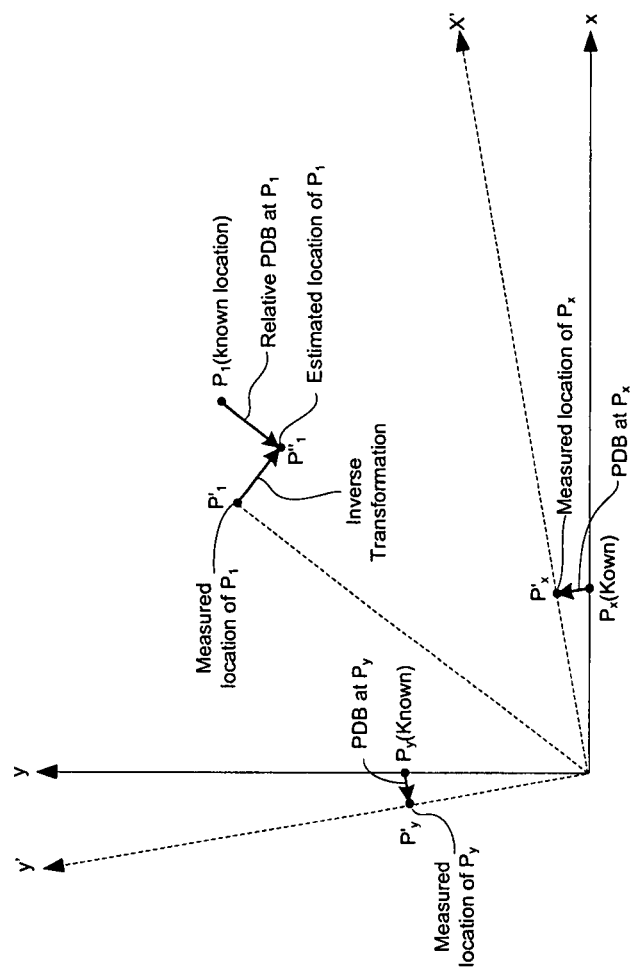
FIG. 5 illustrates the determination of position-dependent bias in a tracking system in one embodiment.

FIG. 5 illustrates the determination of position-dependent bias in a tracking system in one embodiment. FIG. 5 illustrates only two dimensions to facilitate visualization. It will be appreciated that the features illustrated in FIG. 5 can be generalized to a 3D coordinate space. In FIG. 5, two fiducial points Px and Py have known positions in a reference coordinate system x-y, such as the coordinate system established by the interoperative x-ray imaging system described above. Point P'x represents the measured location of Px in a tracking coordinate system (e.g., a tracking coordinate system established by one of the tracking systems described above). Similarly, point P'y represents the measured location of point Py in the tracking coordinate system. It is assumed that points Px and Py are close enough in spatial extent to have approximately the same magnitude of position-dependent bias.

A rigid transformation between the points (Px,Py) and the points (P'x,P'y) may then be calculated. The transformation may be applied to any point in the reference coordinate system to map it to a point in the tracking coordinate system. Conversely, the inverse transformation may be applied to the measured location of a point in the tracking coordinate system to map that point to a location in the reference coordinate system. In FIG. 5, the measured location of P1 in the tracking coordinate system (P1') is mapped to an estimated location of P1 in the reference coordinate system (P1") by applying the inverse transformation as described above.

If there were no relative position-dependent bias in the tracking system between the fiducial points Px and Py, and the fiducial point P1, then the estimated location of P1 (P1") determined by the inverse transformation would be an accurate estimate of the location of P1. An error between the estimated location of P1 (P1") and the known location of P1 in the reference coordinate system provides a measure of the relative position-dependent bias. This error is illustrated by the relative position-dependent bias (PDB) vector between P1 and P1" in FIG. 6.

This procedure may be repeated for a multiplicity of different P1 points to create a map of position-dependent biases over a region of interest in the tracking coordinate system (e.g., the expected area of surgical treatment). Alternatively, the results at a limited number of different P1 points bounding a region of interest in the tracking coordinate system may be linearly interpolated to the centroid of the reference fiducial markers Px and Py, and superimposed to create such a map. The methodology described above may be extended to 3-dimensional space, using a minimum of three fiducial markers to define a 3D rigid transformation, again assuming that the fiducial points are small enough in spatial extent to assume that they all have approximately the same bias. The results of the mapping may be stored in a control system and used to generate signals that control a positioning system (e.g., a robotic surgical couch or a robotic surgical instrument) that corrects for the position-dependent bias of the tracking system and conforms the surgical treatment to a pre-operative treatment plan.

Figure 6:
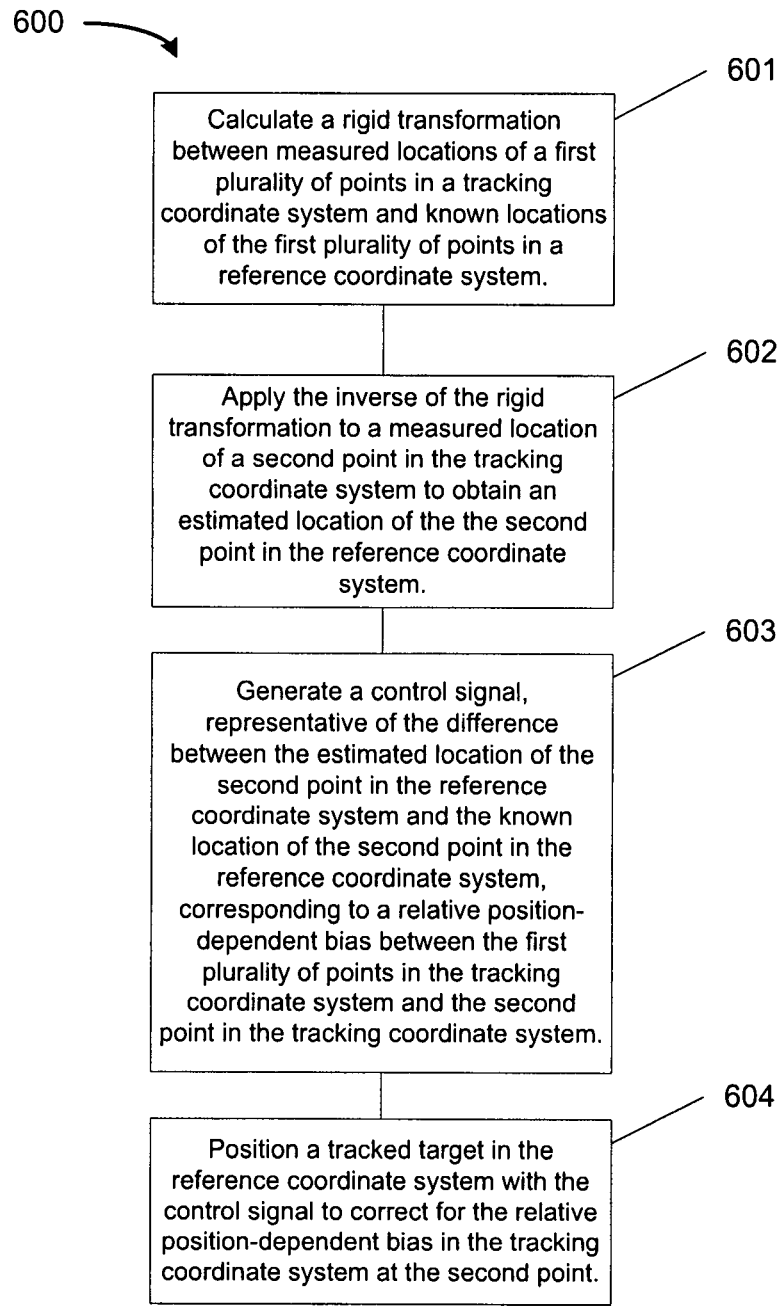
FIG. 6 is a flowchart illustrating a method for removing position-dependent bias in a tracking system in one embodiment.

FIG. 6 is a flowchart 600 illustrating the method described above in one embodiment. In operation 601, a rigid transformation is calculated between the known locations of a plurality of points (e.g., fiducial points) in a reference coordinate system and the measured locations of the plurality of points in a tracking coordinate system. In operation 602, the inverse of the rigid transformation is applied to the measured location of an other point in the tracking coordinate system to obtain an estimate of the location of the other point in the reference coordinate system. In operation 603, the difference between the estimated location of the other point and the known location of the other point may be used to generate a control signal representative of that difference, and corresponding to the relative position-dependent bias between the plurality of points and the other point. In operation 604, the control signal may be used to position a tracked target or instrument in the reference coordinate system to correct for the relative position-dependent bias at the other point. As noted above, operations 601 through 603 may be repeated at a number of different other points around or over a region of interest to generate a direct or interpolated map of relative position-dependent bias over the region of interest.

Figure 7:
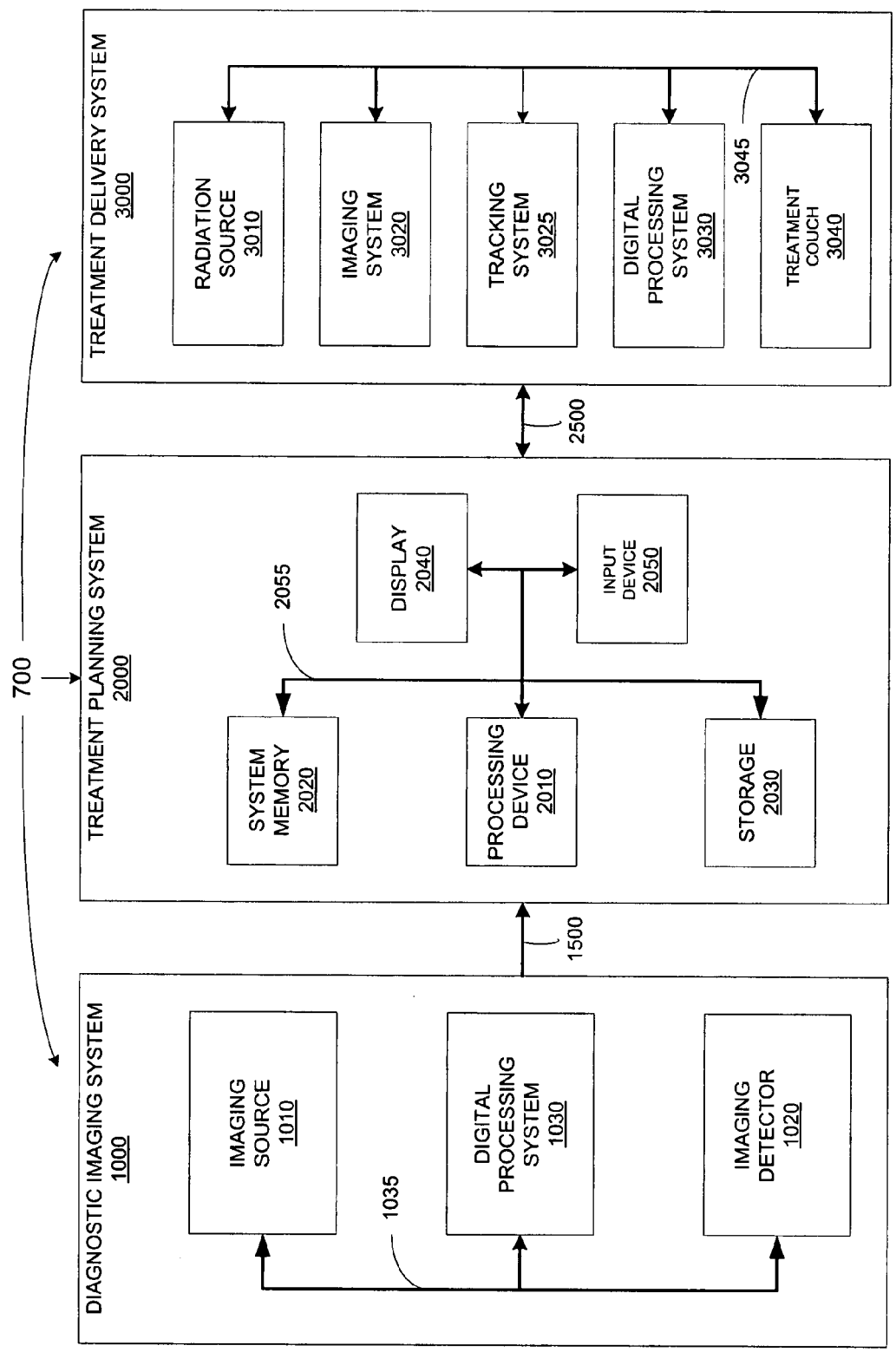
FIG. 7 illustrates a system in which embodiments of the invention may be implemented.

FIG. 7 illustrates one embodiment of systems 700 that may be used in performing surgical and/or therapeutic treatment in which embodiments of the present invention may be implemented. As described below and illustrated in FIG. 7, system 700 may include a diagnostic imaging system 1000, a treatment planning system 2000 and a treatment delivery system 3000.

Diagnostic imaging system 1000 may be any system capable of producing medical diagnostic images of a patient that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 is discussed at times in relation to a CT imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning and/or image processing operations discussed herein, such as the spine segmentation tool described herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein and/or for storing 3D imaging data and DRRs as discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 may include a therapeutic and/or surgical radiation source 3010 (or alternatively, a robotically-controlled invasive surgical instrument, not shown) to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a tracking system 3025 as described herein. Treatment delivery system 3000 may also include a digital processing system 3030 to control radiation source 3010, imaging system 3020, tracking system 3025 and a patient support device such as a treatment couch 3040. Digital processing system 3030 may be configured to register 2D radiographic images from imaging system 3020, from two or more stereoscopic projections, with digitally reconstructed radiographs (e.g., DRRs from segmented 3D imaging data) generated by digital processing system 1030 in diagnostic imaging system 1000 and/or DRRs generated by processing device 2010 in treatment planning system 2000. Digital processing system 3030 may also be configured to compute rigid transformations between imaging system 3020 and tracking system 3025, to calculate position-dependent biases in tracking system 3025 and to generate control signals to control the relative positions of robotic treatment couch 3040, radiation source 3010 or other surgical instrumentation. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020, tracking system 3025 and treatment couch 3040 by a bus 3045 or other type of control and communication interface.

Digital processing system 3030 may implement methods (e.g., such as method 600 described above) to correct for position-dependent bias in tracking system 3025 in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray Incorporated of California, or be another type of conventional treatment table known to those of ordinary skill in the art.

Alternatively, treatment delivery system 3000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient.

Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as robotic manufacturing or machine-vision systems, for example. In such applications, for example, "treatment" may refer generally to the effectuation of an operation controlled by the treatment planning system, such as the application of a beam (e.g., radiation, acoustic, etc.) and "target" may refer to a non-anatomical object or area.

Embodiments of the present invention include various operations, which are described herein. These operations may be performed by hardware components, software, firmware or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

It will be apparent from the foregoing description that aspects of the present invention may be embodied, at least in part, in software. That is, the techniques may be carried out in a computer system or other data processing system in response to its processor, such as processing device 2010, for example, executing sequences of instructions contained in a memory, such as system memory 2020, for example. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 2010.

A machine-readable medium can be used to store software and data which when executed by a data processing system causes the system to perform various methods of the present invention. This executable software and data may be stored in various places including, for example, system memory 2020 and storage 2030 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method of calibrating a system used in a medical procedure, comprising:
    tracking, using a tracking system, an object with features of known relative geometry in a tracking coordinate system;
    comparing a measured geometry of the features with the known geometry of the features; and
    determining, using a processing device, the relative position-dependent bias of the tracking system based on the comparing, wherein the relative position-dependent bias is a temporally constant, spatially varying error.

2. The method of claim 1, wherein tracking the object comprises:
    calculating an invertible transformation between known locations of a first plurality of points in a reference coordinate system and measured locations of the first plurality of points in the tracking coordinate system; and
    wherein comparing the measured geometry with the known geometry comprises:
    applying an inverse of the invertible transformation to a measured location of a second point in the tracking coordinate system to obtain an estimated location of the second point in the reference coordinate system; and
    generating a control signal representative of a difference between the estimated location of the second point in the reference coordinate system and a known location of the second point in the reference coordinate system, the difference corresponding to a relative position-dependent bias between the first plurality of points in the tracking coordinate system and the second point in the tracking coordinate system.

3. The method of claim 2, further comprising positioning a tracked surgical instrument in the reference coordinate system with the control signal to correct for the relative position-dependent bias in the tracking coordinate system.

4. The method of claim 2, further comprising positioning a tracked surgical target in the reference coordinate system with the control signal to correct for the relative position-dependent bias in the tracking coordinate system.

5. The method of claim 2, wherein the first plurality of points comprises a first plurality of fiducial markers and the second point comprises a second fiducial marker, wherein the first plurality of fiducial markers and the second fiducial marker are positioned at known locations on the object.

6. The method of claim 5, wherein the object defines the reference coordinate system.

7. The method of claim 5, wherein the reference coordinate system comprises an x-ray imaging system.

8. The method of claim 2, further comprising:
    determining the known locations of the first plurality of points in the reference coordinate system and the known location of the second point in the reference coordinate system;
    measuring the locations of the first plurality of points in the tracking coordinate system; and
    measuring the location of the second point in the tracking coordinate system.

9. The method of claim 2, further comprising determining the relative position-dependent bias for a plurality of different second points over a region of interest in the tracking coordinate system to generate a map of relative position-dependent bias over the region of interest in the tracking coordinate system.

10. The method of claim 2, further comprising:
    determining the relative position-dependent bias for a plurality of different second points bounding a region of interest in the tracking coordinate system; and
    linearly interpolating the relative position-dependent bias between each of the plurality of different second points and a centroid of the first plurality of points.

* * * * *